's Patent [19]

Gerrit

[11] Patent Number: 4,481,474
[45] Date of Patent: Nov. 6, 1984

[54] DEVICE FOR MEASUREMENT OF THE POTENTIAL WITH RESPECT TO THE SOIL OF A CATHODICALLY PROTECTED METALLIC STRUCTURE

[75] Inventor: Woudstra Gerrit, Roden, Netherlands

[73] Assignee: N.V. Nederlandse Gasunie, Groningen, Netherlands

[21] Appl. No.: 312,986

[22] Filed: Oct. 20, 1981

[30] Foreign Application Priority Data

Jun. 26, 1981 [NL] Netherlands .......................... 8103088

[51] Int. Cl.³ ............................................ G01N 27/42
[52] U.S. Cl. ............................... 324/425; 324/65 CR; 324/71.2; 204/196
[58] Field of Search ................ 324/65 P, 65 CP, 71.1, 324/71.2, 425, 357, 347, 348, 65 CR, 72; 73/86; 204/196, 280, 404

[56] References Cited

U.S. PATENT DOCUMENTS 3,192,144  6/1965  Heuze .................................... 204/196
3,616,415  10/1971  Watson et al. ...................... 324/71.2

FOREIGN PATENT DOCUMENTS 155553  3/1954  Australia ............................. 324/425
2241648  8/1972  Fed. Rep. of Germany .
149011  11/1979  Japan ................................... 324/348

Primary Examiner—Michael J. Tokar
Assistant Examiner—Kevin D. O'Shea
Attorney, Agent, or Firm—Cushman, Darby & Cushman

[57] ABSTRACT

A measuring device for measuring the potential, relative to the earth, of a metallic structure buried in the earth, and cathodically protected by an externally applied DC voltage. The measuring device includes the combination of a metallic, rod-shaped probe adapted to be driven into the earth, a major portion of which is coated with an electrically insulating material. A small portion of the probe near the bottom end thereof is left uncoated and constitutes a measuring electrode. A reference electrode is situated in a transverse bore near the bottom end of the probe, and is electrically insulated therefrom. The probe is adapted to be electrically connected to the metallic structure, for measurement of and the potential difference between the measuring and reference electrodes.

5 Claims, 2 Drawing Figures

DEVICE FOR MEASUREMENT OF THE POTENTIAL WITH RESPECT TO THE SOIL OF A CATHODICALLY PROTECTED METALLIC STRUCTURE

BACKGROUND OF THE INVENTION

This invention relates to a measuring device for measuring the potential of an underground metallic structure, which is cathodically protected by means of an externally applied DC voltage, relative to the earth or soil in which it is situated.

Cathodic protection is used as one method for combating corrosion of metallic structures, such as pipelines, thanks, cables, piers, and the like, which are at least partially buried in the earth. Cathodic protection is accomplished by raising the potential of the surrounding earth by means of introducing a direct current into the earth at a sufficient potential to protect the metal surface. This can be achieved by burying electrodes in the earth at the required distance from the structure in order to obtain a proper current distribution to the metal surfaces to be protected. Cathodic protection is applicable to structures made from all the usual metallic materials of construction such as steel, aluminum, copper, zinc and alloys thereof. As an example, it may be mentioned that, depending on the type of earth in which a cathodically protected structure made of ordinary steel is situated, the potential of the structure, measured relative to a Cu/CuSO4 reference electrode placed in the soil must be −850 mV to −950 mV or lower in order to effectively prevent corrosion.

To insure the continuing proper operation of such a cathodic protection system, this potential should be checked regularly by means of measurement against a reference electrode. However, direct measurement of the voltage difference between the protected structure and the reference electrode is not always reliable, due to the voltage drop in the earth caused by the passage either of the applied protective current or of possible stray currents derived from nearby electrical installations, and the correct potential of the structure with respect to the earth would not then be measured.

The reliability of the potential measurement can be improved by using a measuring electrode electrically connected to the structure, and positioning the measuring electrode and reference electrode with respect to one another in such a way that no extra voltage difference is produced between them by the passage of extraneous currents through the soil. This can be achieved by a measuring rod provided with both a measuring electrode and a reference electrode, and a measuring circuit to measure the potential difference between the measuring electrode and the reference electrode. The measuring rod is adapted to be driven into the soil near the cathodically protected structure, and the measuring electrode is electrically connected to the protected metallic structure.

Such a device for the measurement of the protection potential is known from German Patent Application No. 2,241,648 (laid open for public inspection). In the measuring rod there described, a measuring electrode (in this case a sintered nickel disk impregnated with mercury) and a Cu/CuSo4 reference electrode are placed in close proximity, but electrically insulated from one another, in a protective steel tube which is provided with a sharp tip so that it can be driven into the soil. Openings are provided in the wall of the tube near the electrodes so that the electrodes can come into contact with the surrounding soil.

This known device, however, has the disadvantage that because the contact surfaces where the soil meets the electrodes are situated inside the protective tube, the good contact between the soil and the electrodes necessary for a reliable measurement is not always obtained, so that the measurements may be unreliable. Furthermore, the openings in the wall of the tube must be carefully cleaned after each time the measuring rod is used, which is inconvenient. Moreover, the construction of this known measuring rod is relatively complicated and hence liable to malfunction, for instance, the electrode can slip out of place in the tube without this being noticed immediately.

SUMMARY OF THE INVENTION

The object of the present invention is to provide a measuring device which does not display the above-noted disadvantages. A further objective of this invention is to provide a measuring device which is simpler in both construction and operation relative to known measuring devices, and provides more consistent and reliable measurements.

These and other objectives are accomplished by the measuring device of the present invention, which is comprised of a measuring rod consisting of a rod-shaped metallic probe covered with a layer of electrically insulating material over most of its length, leaving a small part thereof uncoated near the end to be driven into the earth. The uncoated portion of the rod-shaped probe constitutes the measuring electrode. The reference electrode is situated in a transverse bore in the rod-shaped probe near the end driven into the earth, and is electrically insulated from the probe. Preferably, the transverse bore is situated in the uncoated portion of the rod-shaped probe, so that the surface of the reference electrode lies within the surface of the measuring electrode. Means are provided for electrically connecting the measuring electrode to the cathodically protected metallic structure, and for connecting the measuring electrode and reference electrode to a measuring circuit for measuring the potential difference between the respective electrodes. Preferably, the rod-shaped metallic probe is made from the same metal or alloy as the metallic structure the potential of which is to be measured. Suitable materials for coating the metallic rod-shaped probe are, e.g., polyvinylchloride, sintered polyethylene and various epoxy resins.

A dry electrode is preferably used as the reference electrode, in that under the fairly rough conditions under which such a measuring rod may be expected to be used, such a dry electrode is less liable to malfunction than the customary Cu/CuSo4 reference electrode with liquid electrolyte. Such a Cu/CuSo4 reference electrode is customarily used in in situ electrodes because of its highly constant properties. However, when a dry electrode is used, it can be calibrated against a Cu/CuSo4 reference electrode prior to use.

Particularly suitable as a reference electrode in the measuring device of the present invention is a zinc-plaster of Paris electrode in which a zinc electrode is sealed and enclosed in the transverse bore by a layer of plaster of Paris. The porous plaster of Paris, which must be moist when in use, is thereby situated between the zinc electrode and the soil, and combines the function realized by the electrolyte and the porous diaphragm customarily employed in "wet" reference electrodes. However, other dry reference electrodes can also be used. For instance, a dry plaster of Paris/copper sulphateplaster of Paris electrode, wherein the electrode consists of a plaster of Paris/copper sulphate mixture, sealed and enclosed in the transverse bore by a layer of plaster of Paris, has also been found to be highly suitable. Lead or antimony reference electrodes may also be used.

When the measuring rod is being driven into the soil, cabels or pipes present in the vicinity could be damaged. In order to avoid this, the measuring rod can be provided with an essentially conical tip made of plastic, preferably polytetrafluorethylene.

DETAILED DESCRIPTION OF A PREFERRED EMBODIMENT

A preferred embodiment of the invention will be described with reference to the drawings and an example of a typical set-up in which the measuring device of the invention can be utilized.

Figure 1:
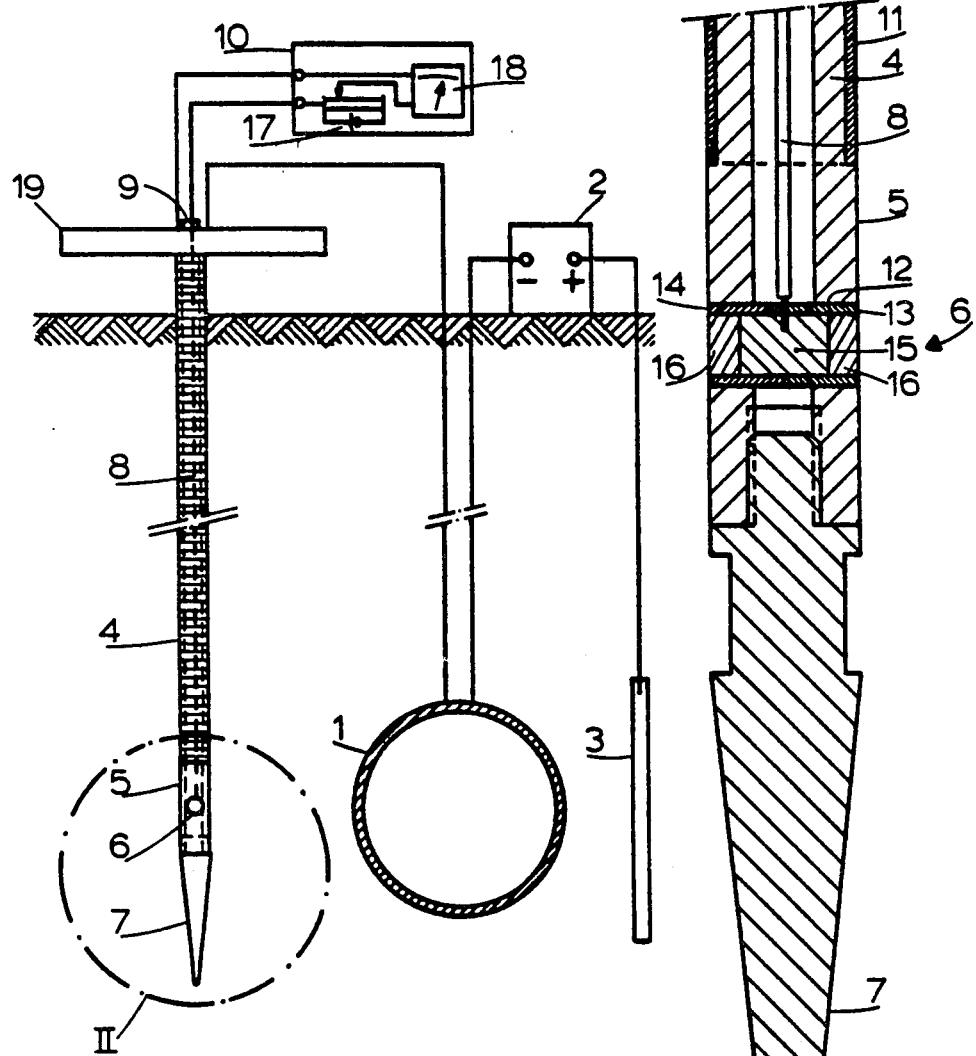
FIG. 1 is a schematic view of a measuring set-up with a measuring device according to the invention for monitoring and installation for cathodic protection.

Referring first to FIG. 1, pipeline 1 is an underground steel pipeline covered with a protective, electrically insulating coating (not shown in the figure). Pipeline 1 is moreover cathodically protected by means of installation 2, which gives the pipeline a negative voltage with respect to the in situ anode 3, also embedded in the soil. In order to check or monitor the operation of the cathodic protection locally, a measuring device according to the present invention is used to measure the potential of the pipe with respect to the soil at the desired located. For this purpose, a conducting metallic rod-shaped probe 4 is driven into the soil, for instance, 50 cm from the center line of pipeline 1 and is connected electrically to pipeline 1. The rod-shaped probe 4 consists of a metallic tube and is covered with a layer of insulating material with the exception of a small portion 5 near the end, which is left bare and constitutes the measuring electrode. Rod-shaped probe 4 is driven into the soil a distance such that the bare portion or measuring electrode 5 is at the same level as pipeline 1. A reference electrode 6 is positioned in a radial bore roughly in the middle of the measuring electrode 5 and is connected via cable 8, through insulating bushing 9, to measuring circuit 10. The rod-shaped probe 4, and hence measuring electrode 5, is also connected to measuring circuit 10, which measures the potential difference between measuring electrode 5 and reference electrode 6.

In the embodiment illustrated, the measuring rod is provided with a polytetrafluorethylene tip 7 to avoid damaging cables or pipes located in the soil when the measuring rod is being driven in. The measuring rod illustrated is further provided with transverse bar 19 which can be used as a handle for driving the measuring rod into the soil or pulling it out.

Figure 2:
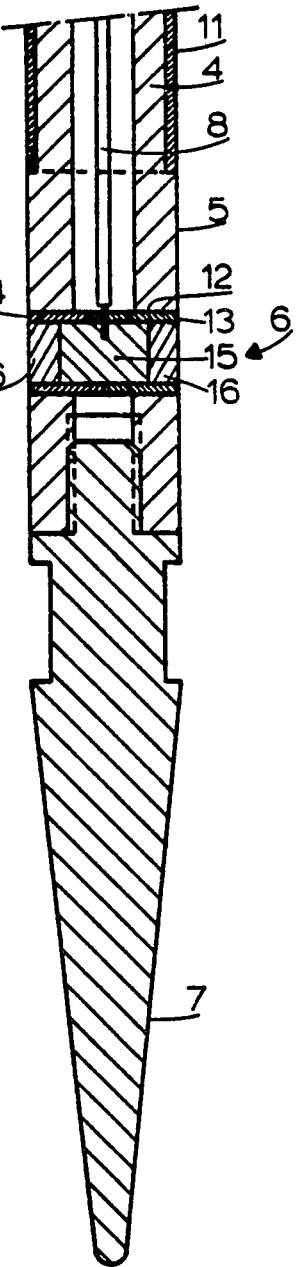
FIG. 2 is a longitudinal section showing in greater detail the lower portion of the measuring rod, which is circled and labeled as Part II in FIG. 1.

FIG. 2 shows the end of the measuring rod or probe in greater detail. Parts 4, 5, 7, and 8 are as previously discussed in connection with FIG. 1. Insulating layer 11 covers most of the length of the rod-shaped probe.

Reference electrode 6 is positioned in bore 12 shown as extending through the bare, measuring electrode portion 5 of the probe. Reference electrode 6 is insulated from the metallic probe by means of two insulating bushings 13 and 14. In this instance, the reference electrode is a zinc-plaster of Paris electrode consisting of a small cylinder of zinc 15, enclosed between plaster of Paris plugs 16.

Prior to each use of the measuring device, it is calibrated with reference to a $Cu/CuSo_4$ electrode. To carry out this calibration, the $Cu/CuSo_4$ electrode is placed in the soil, and the measuring electrode or rod is connected to the $Cu/CuSo_4$ electrode instead of to pipeline 1. The reading of measuring instrument 18 is then set to zero by means of an adjustable voltage source 17 shown in FIG. 1. Although measuring instrument 18 is symbolically shown as a dial instrument, instruments having a digital readout can also be used in circuit 10. Moreover, although adjustable voltage source 17 is here symbolically shown as a potentiometer circuit with a battery, any suitable type of adjustable constant-voltage source can be used for this purpose.

Prior to driving the measuring rod into the soil, it is recommended that measuring electrode 5 be abraded to remove any oxide layer that may have formed thereon. If this is done, the settling time required for the measuring electrode to reach the correct potential amounts to only a few minutes.

What is claimed is:

1. A measuring device for measuring the potential, relative to the earth, of a metallic structure at least partially buried in said earth and cathodically protected by an externally applied DC voltage, comprising in combination:

a metallic, rod-shaped probe, having one end provided with an essentially conical tip for being driven into said earth, and having a major portion of the surface of said probe coated with an electrically insulating material, and a minor portion of said surface, near said one end, not coated with said insulating material, said uncoated portion constituting a measuring electrode;

a dry reference electrode consisting of (a) a material selected from the group consisting of zinc-plaster of Paris and (b) plaster of Paris/copper sulfateplaster of Paris, situated in a transverse bore in the rod-shaped probe near one end, and electrically insulated from said probe;

said measuring device having means for electrically connecting said measuring electrode to said metallic structure, and means for electrically connecting said measuring electrode and said reference electrode to a measuring circuit for measuring the potential difference between said measuring and reference electrodes.

2. The measuring device of claim 1 additionally including a measuring circuit and means connecting said measuring electrode and said reference electrode to said measuring circuit.

3. The measuring device of claim 1 or 2 wherein said transverse bore is located in said uncoated measuring electrode portion of said rod-shaped probe.

4. The measuring device of claim 1 or 2 wherein said essentially conical tip is made of plastic.

5. The measuring device of claim 4 wherein said conical tip is made essentially of polytetrafluorethylene.

* * * * *

UNITED STATES PATENT AND TRADEMARK OFFICE
CERTIFICATE OF CORRECTION

PATENT NO. : 4,481,474
DATED : November 6, 1984
INVENTOR(S) : Gerrit WOUDSTRA

It is certified that error appears in the above—identified patent and that said Letters Patent is hereby corrected as shown below:

On the title page;

[75] Inventor: Delete "Woudstra Gerrit" and insert

--Gerrit Woudstra--.

Signed and Sealed this

Fifteenth Day of October 1985

[SEAL]

Attest:

Attesting Officer

DONALD J. QUIGG

Commissioner of Patents and Trademarks—Designate